United States Patent
Patil et al.

(10) Patent No.: US 10,711,216 B2
(45) Date of Patent: *Jul. 14, 2020

(54) ESTER COMPOUNDS, LUBRICATING OIL COMPOUNDS CONTAINING SAME AND PROCESSES FOR MAKING SAME

(71) Applicant: ExxonMobil Chemical Patents Inc., Baytown, TX (US)

(72) Inventors: Abhimanyu O. Patil, Westfield, NJ (US); Kyle G. Lewis, Houston, TX (US); Satish Bodige, Wayne, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/032,324

(22) Filed: Jul. 11, 2018

(65) Prior Publication Data

US 2019/0100710 A1    Apr. 4, 2019

Related U.S. Application Data

(60) Provisional application No. 62/565,548, filed on Sep. 29, 2017.

(51) Int. Cl.
| | |
|---|---|
| *C10M 105/34* | (2006.01) |
| *C07C 69/003* | (2006.01) |
| *C07C 69/007* | (2006.01) |
| *C07C 67/08* | (2006.01) |
| *C07C 69/612* | (2006.01) |
| *C07C 29/147* | (2006.01) |
| *C07C 69/75* | (2006.01) |
| *C07C 69/14* | (2006.01) |
| *C07C 69/78* | (2006.01) |
| *C07C 51/14* | (2006.01) |
| *C07C 2/34* | (2006.01) |
| *C07C 69/614* | (2006.01) |
| *C07C 69/24* | (2006.01) |
| *C07C 69/76* | (2006.01) |

(52) U.S. Cl.
CPC ............ *C10M 105/34* (2013.01); *C07C 2/34* (2013.01); *C07C 29/147* (2013.01); *C07C 51/14* (2013.01); *C07C 67/08* (2013.01); *C07C 69/003* (2013.01); *C07C 69/007* (2013.01); *C07C 69/14* (2013.01); *C07C 69/24* (2013.01); *C07C 69/612* (2013.01); *C07C 69/614* (2013.01); *C07C 69/75* (2013.01); *C07C 69/76* (2013.01); *C07C 69/78* (2013.01); *C10M 2207/2815* (2013.01); *C10N 2220/022* (2013.01); *C10N 2220/028* (2013.01); *C10N 2230/02* (2013.01); *C10N 2230/10* (2013.01)

(58) Field of Classification Search
CPC .......... C07C 51/14; C07C 2/34; C07C 69/78; C07C 69/76; C07C 69/75; C07C 69/614; C07C 69/612; C07C 69/003; C07C 69/007; C07C 67/08; C07C 29/147; C07C 69/14; C07C 69/24; C07C 11/02; C07C 53/128; C07C 31/125; C10N 2220/022; C10N 2220/028; C10N 2230/10; C10N 2230/02; C10M 2207/2815
See application file for complete search history.

(56) References Cited

U.S. PATENT DOCUMENTS

| | | |
|---|---|---|
| 2,460,182 A | 1/1949 | Geigy |
| 3,059,007 A | 12/1962 | Vos et al. |
| 3,910,963 A | 10/1975 | Souma et al. |
| 4,126,585 A | 11/1978 | Conrad et al. |
| 4,332,738 A | 6/1982 | Benitez et al. |
| 4,658,078 A | 4/1987 | Slaugh et al. |
| 5,646,332 A | 7/1997 | Cusumano et al. |
| 6,239,318 B1 | 5/2001 | Schuler et al. |
| 2010/0261628 A1* | 10/2010 | Scherer ............... C10M 105/34 508/496 |
| 2011/0084243 A1 | 4/2011 | Cranor et al. |
| 2014/0011086 A1 | 1/2014 | Fujdala et al. |
| 2015/0284350 A1 | 10/2015 | Aruleswaran et al. |
| 2017/0183596 A1 | 6/2017 | Ng et al. |
| 2018/0119045 A1 | 5/2018 | Patil et al. |

FOREIGN PATENT DOCUMENTS

| | | |
|---|---|---|
| DE | 10 2013 009323 A | 12/2014 |
| EP | 0629603 | 12/1994 |
| EP | 2474537 | 7/2012 |
| JP | H0782216 | 3/1995 |
| WO | 2005/049542 | 6/2005 |

OTHER PUBLICATIONS

Sarnayskaya, et al., "Volatility and thermooxidation stability of synthetic ester oils," Khimiya I Tekhnologiya Topliv I Masel, 1975, vol. 10, pp. 49-52 (Abstract).

Pincock et al., "Alkylation of Ethyl, Isobornyl, and Menthyl Esters of 2- Methyibutanoic Acid,"Journal of Organic Chemistry, 1964, vol. 29, No. 10, pp. 299-2992.

Pirozhkov et al., "Synthesis of allyl esters of neo acids," Zhurnal Prikiadnoi Khimii, 1976, vol. 49, No. 7, pp. 1646-1648 (Abstract).

Shapovalov, et al., "Radiation-induced telomerization of ethylene with methyl propionate," Deposited Doc., Viniti, 1975, vol. 32, No. 8, pp. 1628-1675 (Abstract).

(Continued)

*Primary Examiner* — Vishal V Vasisth

(57) ABSTRACT

This disclosure relates to ester compounds derived from neo-alcohol, lubricating oil base stocks comprising such ester compounds, lubricating oil compositions comprising such ester compounds, and method for making such compounds and/or base stocks. The lubricating oil base stocks comprising the ester compounds exhibit desirable lubricating properties such as polarity and oxidation stability.

25 Claims, No Drawings

(56) References Cited

OTHER PUBLICATIONS

Ye et al., "Nickel-catalyzed directed sulfenylation of sp2 and sp3 C—H bonds," Chemical Communications, 2015, vol. 51, No. 37, pp. 7863-7866.

Prout et al., "Unsymemetrical Quaternary Carbon Compounds. III. The Preparation and Resolution of Trialkylacetic Acids," Journal of Organic Chemistry, 1960, vol. 25, No. 5, pp. 835-838.

U.S. Appl. No. 15/988,716, filed May 24, 2018 Patil et al.

Didomenico et al., "Compounds containing quaternary carbons, their use in medical devices, and methods," PCT Int. Appl., 2003.

Wagner-Jauregg et al., "Cycloalkyl aliphatic acids and their chemotherapeutic trial in leprosy and tuberculosis," Arb. Staatl. Inst. Exptl. Therap. U. Forsch.-Inst, Chemotherap. 1939, Frankfurt, No. 37, pp. 22-27, From: Chem. Zentr., 1939, II, pp. 459-460.

Mndzhoyan et al., "Derivatives of substituted acetic acids, XIX. Synthesis of .beta.-substituted phenylethyl esters of dialkylaminoacetic acids," Doklady Akademii Nauk Armyanskoi SSR, 1959, vol. 29, pp. 235-243.

Re et al., "Cyclization of 3-carboxy-3,6-dimethyl-1,5-heptadiene, a terpene acid with the skeleton of Artemisia ketone," Helvetica Chirnica Acta, 1958, vol. 41, pp. 1695-1709.

U.S. Appl. No. 62/565,536, filed Sep. 29, 2017 Patil et al.

Kanth et al., "Selective Reduction of Carboxylic Acids into Alcohols Using NaBH4 and I2," J. Org. Chem., 1991, vol. 56, pp. 5964-5965.

Prasad et al., "Convenient Methods for the Reduction of Amides, Nitriles, Carboxylic Esters, Acids and Hydroboration of Alkenes Using NaBH4/I2 System," Tetrahedron, 1992, vol. 48, No. 22, pp. 4623-4628.

Jirosova et al., "Sphinganine-Like Biogenesis of (E)-1-Nitropentadec-1-ene in Termite Solders of the Genus Prorhinotermes," Chembiochem—a European Journal of Chemical Biology, 2014, vol. 15, No. 4, pp. 533-536.

Luo et al., "Comparative study on aroma compounds in Chinese-type and Japanese-type soy sauces,".

Achonduh et al., "From alkenes to alcohols by cobalt-catalyzed hydroformylation-reduction," Tetrahedron, 2015, vol. 71, No. 8, pp. 1241-1246.

Cho et al., "Facile Reduction of Carboxylic Acids, Esters, Acid Chlorides, Amides and Nitriles to Alcohols or Amines Using NaBH4/BF3.Et20," Bulletin of the Korean Chemical Society, 2004, pp. 407-409.

Lebedev et al., "Synthesis of branched carboxylic acids with .alpha.-olefins and carbon monoxide in the presence of boron fluoride dehydrate," Neftepererabotka I Neftekhimiya, 1972, No. 8, pp. 7-11.

Polgar et al., "Long-Chain Acids Containing a Quaternary Carbon Atom, Part II," Journal of the American Chemical Society. 1943, pp. 615-619.

Delrnau et al., "Combined Extraction of Cesium and Strontium from Alkaline Nitrate Solutions," Solvent Extraction and Ion Exchange, 2006, vol. 24, No. 2, pp. 197-217.

Rautenstrauch, "Potassium carboxylates by direct carbonylation of potassium alkoxides," Helvetica Chimica Acta, 1987, vol. 70, No. 3, pp. 593-599.

Newman, "alpha, alpha-Di-t-butyl-beta-propiolactone and Methyldi-t- butylacetic Acid from Di-t-butylketene," The Journal of Organic Chemistry, 1968, pp. 2144-2145.

Asano et al., "Syntheses of branched-chain fatty acids contained in tubercle bacilli. VI. Phthioic acid. 4," Yakugaku Zasshi, 1945, vol. 65, No. 4A, pp. 15-17.

Churilova et al., "Telomerization of propylene with carboxylic acids," Izvestiya Akademii Nauk SSSR, Seriya Khimicheskaya, 1975, vol. 11, pp. 2497-2501.

Stallberg-Stenhagen, "Optically active higher aliphatic compounds. XI. The synthesis of (–)-2-methyl-2-ethyieicosanoic acid," Arkiv Foer Kemi, 1951, vol. 3, pp. 273-280.

Bondareva et al., "Synthesis and extracting properties of triacylated ethyleneamines," Russian Journal of Applied Chemistry, 2011, vol. 84, No. 11, pp. 1897-1902.

Eidus et al., "Carbonylation of pentene-1 and 3-methylbutene-1 by carbon monoxide in the presence of hydrates of boron trifluoride," Bulletin of the Academy of Sciences of the USSR Division of Chemical Science, 1970, pp. 1585-1587.

U.S. Appl. No. 15/988,683, filed May 24, 2018 Chen et al.

\* cited by examiner

ESTER COMPOUNDS, LUBRICATING OIL COMPOSITIONS CONTAINING SAME AND PROCESSES FOR MAKING SAME

PRIORITY CLAIM

This application claims priority to and the benefit of U.S. Ser. No. 62/565,548, filed Sep. 29, 2018, the content of which is incorporated herein by reference in its entirety.

FIELD OF THE DISCLOSURE

This disclosure relates to esters compounds, lubricating oil base stocks, lubricating oil compositions, and processes for making them. In particular, this disclosure relates to ester compounds of neo-alcohols, lubricating oil base stocks and lubricating oil compositions comprising such ester compounds, and processes for making them.

BACKGROUND OF THE DISCLOSURE

Lubricants in commercial use today are prepared from a variety of natural and synthetic base stocks admixed with various additive packages and solvents depending upon their intended application. The base stocks typically include mineral oils, polyalpha-olefins (PAO), gas-to-liquid (GTL) base oils, silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

Polyalpha-olefins (PAOs) are important lubricant base stocks with many excellent lubricant properties, including high viscosity index (VI), low volatility and are available in various viscosity range (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lubricant formulators usually add one or multiple polar co-base stocks. Ester or alkylated naphthalene (AN) is usually present at 1 to 50 wt % levels in many finished lubricant formulations to increase the fluid polarity which improves the solubility of polar additives and sludge. Furthermore, high oxidation stability is generally desirable for a base stock in order to impart a long service life to engine oils.

Aliphatic neo-polyols comprising at least two hydroxyl groups having a common quaternary carbon atom at the beta-location of the hydroxyl groups in the molecule are known. Esters of such neo-polyols featuring multiple ester groups in the molecule have found use as lubricating oil base stocks. They are known for high-temperature oxidation stability. However, they tend to have very high polarity due to the presence of multiple ester groups in the same molecule, causing issues such as seal compatibility to lubricating formulations containing them.

Therefore, there is a need for polar base stock fluids that provide appropriate solubility and dispersancy for polar additives or sludge generated during service of lubricating oils, desired level of polarity, as well as a high oxidation stability.

This disclosure meets this and other needs.

SUMMARY OF THE DISCLOSURE

It has been found that esters of mono neo-alcohols can be advantageously used as lubricating oil base stocks with desirable lubricating oil properties such as viscosity, volatility, polarity and oxidation stability.

A first aspect of this disclosure relates to a compound having a formula (F-I):

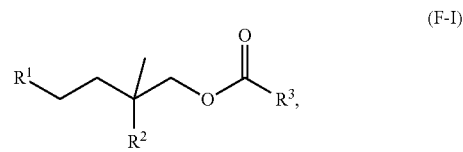

(F-I)

wherein: $R^1$ and $R^2$ are independently each a hydrocarbyl group comprising at least 2 carbon atoms; and $R^3$ is a substituted or unsubstituted hydrocarbyl group.

A second aspect of this disclosure relates to a lubricating oil composition comprising an ester compound of the first aspect of this disclosure.

A third aspect of this disclosure relates to a process for making an ester product comprising an ester compound having a formula (F-I) below:

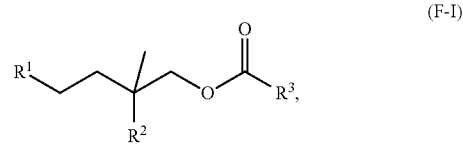

(F-I)

where $R^1$ and $R^2$ are independently each a hydrocarbyl group comprising at least two carbon atoms; and $R^3$ is a substituted or unsubstituted hydrocarbyl group, the process comprising: (I) providing a neo-alcohol having a formula (F-II) below:

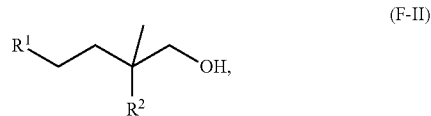

(F-II)

where $R^1$ and $R^2$ are the same as the $R^1$ and $R^2$ in formula (F-I), respectively; (II) reacting the neo-alcohol with an acid having a formula (F-III) below:

(F-III)

where $R^3$ is the same as the $R^3$ in formula (F-I), and/or an anhydride of the acid, in the presence of an acid catalyst to obtain a product mixture; and (III) obtaining the ester compound and/or the lubricating oil base stock from the product mixture.

Further features and advantages of this disclosure will be understood by reference to the following drawings and detailed description.

DETAILED DESCRIPTION OF THE DISCLOSURE

Definitions

In this disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms.

"Cycloalkyl group" refers to an alkyl group in which all carbon atoms form a ring structure. Non-limiting examples of cycloalkyl groups include cyclopentyl, cyclohexyl, decahydronaphthalen-1-yl, spiro[5.5]undecan-3-yl, and the like.

"Aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

"Arylalkyl group" refers to an alkyl group substituted by an aryl group or alkylaryl group. Non-limiting examples of arylalkyl group include benzyl, 2-phenylethyl, 4-phenylbutyl, and the like.

"Alkylaryl group" refers to an aryl group substituted by an alkyl group. Non-limiting examples of alkylaryl group include 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, and the like.

"Cycloalkylalkyl group" refers to an alkyl group substituted by a cycloalkyl group or an alkylcycloalkyl group. An example of cycloalkylalkyl group is cyclohexylmethyl, and the like.

"Alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tert-butylcyclohexyl, and the like.

"Hydrocarbyl group" refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which one or more hydrogen atom is substituted by any another group. An "unsubstituted" hydrocarbyl group is a hydrocarbyl group.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

"Mono-ester" refers to a compound having one ester (—C(O)—O—) functional group therein.

"Di-ester" refers to a compound having two ester (—C(O)—O—) functional groups therein.

"Gamma-branched alcohol" refers to an alcohol having a structure corresponding to the following formula:

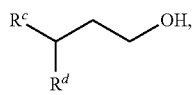

where $R^c$ and $R^d$ are independently any substituted or unsubstituted hydrocarbyl groups preferably comprising from d1 to d2 carbon atoms, where d1 and d2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as d1<d2. More preferably d1=2 and d2=50. Preferably $R^c$ and $R^d$ are alkyl groups. More preferably $R^c$ and $R^d$ are linear or branched alkyl groups. Still more preferably $R^c$ and $R^d$ differ in terms of total number of carbon atoms contained therein by two (2).

"Neo-acid" refers to a carboxylic acid having the following general structure:

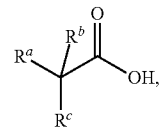

where $R^a$, $R^b$, and $R^c$, the same or different, are independently hydrocarbyl groups.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. Non-limiting examples of lubricating oils include those in liquid form during normal use thereof such as engine oils and gear box oils and those in viscous liquid form during normal use such as grease. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

I. The Neo-Alcohol-Derived Ester Compounds

One aspect of this disclosure is a novel category of compounds having a general formula (F-I) below:

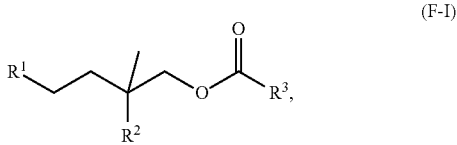

(F-I)

wherein $R^1$ and $R^2$ are each independently a hydrocarbyl group comprising at least 2 carbon atoms therein (preferably a C2 to C60 hydrocarbyl group, more preferably a C2 to C60 alkyl group, still more preferably a C2 to C60 linear or branched alkyl group, still more preferably a C2 to C30 linear or branched alkyl group); and $R^3$ is a substituted or unsubstituted hydrocarbyl group. To the extent this compound can be considered as an ester derived from a neo-alcohol, it will be referred to as such in this disclosure, and also as "ester of this disclosure" herein.

In formula (F-I), preferably, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

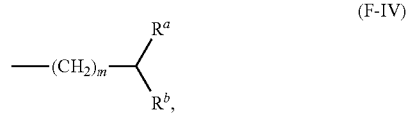

(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably $R^a$ and $R^b$ each independently comprise c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably, the total number of carbon atoms in linear $R^1$ and $R^2$ is an even number. Preferably, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ in formula (F-I) differ, it is highly desirable that they differ in terms of molar mass thereof by no greater than 145 (or 130, 115, 100, 85, 70, 55, 45, 30, or even 15) grams per mole. Preferably, in such cases, $R^1$ and $R^2$ differ in terms of total number of carbon atoms contained therein by no greater than 10 (or 9, 8, 7, 6, 5, 4, 3, 2, or even 1).

$R^3$ can be any substituted or unsubstituted hydrocarbyl group. $R^3$ can preferably comprise up to 60, 50, 40, 30, or 20 carbon atoms. Preferably $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Preferably, $R^3$ is a group selected from (a) linear or branched alkyl group, alkylaryl group, aryl group, arylalkyl group, cycloalkyl group, alkylcycloalkyl group, and cycloalkylalkyl group; and (b) substituted derivatives of those in category (a). Substitution to the category (a) hydrocarbyl groups include, but are not limited to: oxygen-containing groups such as alkoxy groups, nitrogen-containing groups, and the like.

$R^3$ can be preferably an alkyl group, an aryl group, an arylalkyl group, an alkylaryl group, a cycloalkyl group, a cycloalkylalkyl group, or an alkylcycloalkyl group.

Non-limiting examples of $R^3$ as an alkyl group include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof, and the like.

Non-limiting examples of $R^3$ as an aryl group include phenyl, all naphthyls, all phenanthyls, all indenyls, and the like.

Non-limiting examples of $R^3$ as an alkylaryl group include alkyl-substituted phenyls, alkyl-substituted naphthyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

Non-limiting examples of $R^3$ as an arylalkyl group include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl, and the like.

Preferred examples of aromatic $R^3$ groups are: phenyl, benzyl, 2-phenylethyl, 3-phenylpropryl, 4-phenylbutyl, 3-(3-methylphenyl)propyl, 3-(p-tolyl)propyl, 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, 2-methylcyclohexyl, 3-methylcyclohexyl, 4-methylcyclohexyl, 4-tert-butylcyclohexyl, 4-phenylcyclohexyl, cyclohexylpentyl, nitrophenylmethyl, xylylmethyl, xylylpropyl, methoxyphenylethyl, methoxyphenylpropyl, methoxyphenylbutyl, nitrophenylpropyl, nitrophenylbutyl, and xylylbutyl.

Particularly, desirable examples of the ester compounds of this disclosure are as follows, which alone or in various combinations can be advantageously used as a lubricating oil base stock:

2-methyl-2-octyldodecyl acetate, 2-methyl-2-octyldodecyl propanoate, 2-methyl-2-octyldodecyl butanoate, 2-methyl-2-octyldodecyl pentanoate, 2-methyl-2-octyldodecyl hexanoate, 2-methyl-2-octyldodecyl octanoate, 2-methyl-2-octyldodecyl decanoate, 2-methyl-2-octyldodecyl dodecanoate, 2-methyl-2-octyldodecyl tetradecanoate, 2-methyl-2-octyldodecyl hexadecanoate, 2-methyl-2-octyldodecyl octadecanoate, 2-methyl-2-octyldodecyl icosanoate, 2-methyl-2-octyldodecyl benzoate, 2-methyl-2-octyldodecyl 4-methylbenzoate, 2-methyl-2-octyldodecyl 4-ethylbenzoate, 2-methyl-2-octyldodecyl 4-butylbenzoate, 2-methyl-2-octyldodecyl 4-pentylbenzoate, 2-methyl-2-octyldodecyl 4-hexylbenzoate, 2-methyl-2-octyldodecyl 4-heptylbenzoate, 2-methyl-2-octyldodecyl 4-octylbenzoate, 2-methyl-2-octyldodecyl [1,1'-biphenyl]-4-carboxylate, 2-methyl-2-octyldodecyl 1-naphthoate, 2-methyl-2-octyldodecyl 2-naphthoate, 2-methyl-2-octyldodecyl-3-phenylpropanoate, 2-methyl-2-octyldodecyl 2-phenylacetate, 2-methyl-2-octyldodecyl 4-phenylbutanoate, 2-methyl-2-octyldodecyl 5-phenylpentanoate, 2-methyl-2-octyldodecyl 6-phenylhexanoate, 2-methyl-2-octyldodecyl 7-phenylheptanoate; 2-methyl-2-octyldodecyl 2-methylcyclohexane-1-carboxylate, 2-methyl-2-octyldodecyl 3-methylcyclohexane-1-carboxylate, 2-methyl-2-octyldodecyl 4-methylcyclohexane-1-carboxylate, 2-methyl-2-octyldodecyl 4-(tert-butyl)cyclohexane-1-carboxylate, 2-methyl-2-octyldodecyl 4-phenylcyclohexane-1-carboxylate, 2-methyl-2-octyldodecyl 4-pentylcyclohexane-1-carboxylate;

2-butyl-2-methyloctyl acetate, 2-butyl-2-methyloctyl propanoate, 2-butyl-2-methyloctyl butanoate, 2-butyl-2-methyloctyl pentanoate, 2-butyl-2-methyloctyl hexanoate, 2-butyl-2-methyloctyl octanoate, 2-butyl-2-methyloctyl decanoate, 2-butyl-2-methyloctyl dodecanoate, 2-butyl-2-methyloctyl tetradecanoate, 2-butyl-2-methyloctyl hexadecanoate, 2-butyl-2-methyloctyl octadecanoate, 2-butyl-2-methyloctyl icosanoate, 2-butyl-2-methyloctyl benzoate, 2-butyl-2-methyloctyl 4-methylbenzoate, 2-butyl-2-methyloctyl 4-ethylbenzoate, 2-butyl-2-methyloctyl 4-butylbenzoate, 2-butyl-2-methyloctyl 4-pentylbenzoate, 2-butyl-2-methyloctyl 4-hexylbenzoate, 2-butyl-2-methyloctyl 4-heptylbenzoate, 2-butyl-2-methyloctyl 4-octylbenzoate, 2-butyl-2-methyloctyl [1,1'-biphenyl]-4-carboxylate, 2-butyl-2-methyloctyl 1-naphthoate, 2-butyl-2-methyloctyl 2-naphthoate, 2-methyl-2-octyldodecyl-3-phenylpropanoate, 2-butyl-2-methyloctyl 2-phenylacetate, 2-butyl-2-methyloctyl 4-phenylbutanoate, 2-butyl-2-methyloctyl 5-phenylpentanoate, 2-butyl-2-methyloctyl 6-phenylhexanoate, 2-butyl-2-methyloctyl 7-phenylheptanoate, 2-butyl-2-methyloctyl 2-methylcyclohexane-1-carboxylate, 2-butyl-2-methyloctyl 3-methylcyclohexane-1-carboxylate, 2-butyl-2-methyloctyl 4-methylcyclohexane-1-carboxylate, 2-butyl-2-methyloctyl 4-(tert-butyl)cyclohexane-1-carboxylate, 2-butyl-2-methyloctyl 4-phenylcyclohexane-1-carboxylate, 2-butyl-2-methyloctyl 4-pentylcyclohexane-1-carboxylate;

2-hexyl-2-methyldecyl acetate, 2-hexyl-2-methyldecyl propanoate, 2-hexyl-2-methyldecyl butanoate, 2-hexyl-2-methyldecyl pentanoate, 2-hexyl-2-methyldecyl hexanoate, 2-hexyl-2-methyldecyl octanoate, 2-hexyl-2-methyldecyl decanoate, 2-hexyl-2-methyldecyl dodecanoate, 2-hexyl-2-methyldecyl tetradecanoate, 2-hexyl-2-methyldecyl hexadecanoate, 2-hexyl-2-methyldecyl octadecanoate, 2-hexyl-2-methyldecyl icosanoate, 2-hexyl-2-methyldecyl benzoate, 2-hexyl-2-methyldecyl 4-methylbenzoate, 2-hexyl-2-methyldecyl 4-ethylbenzoate, 2-hexyl-2-methyldecyl 4-butylbenzoate 2-hexyl-2-methyldecyl 4-pentylbenzoate, 2-hexyl-2-methyldecyl 4-hexylbenzoate, 2-hexyl-2-methyldecyl 4-heptylbenzoate, 2-hexyl-2-methyldecyl 4-octylbenzoate, 2-hexyl-2-methyldecyl [1,1'-biphenyl]-4-carboxylate, 2-hexyl-2-methyldecyl 1-naphthoate, 2-hexyl-2-methyldecyl 2-naphthoate, 2-hexyl-2-methyldecyl-3-phenylpropanoate, 2-hexyl-2-methyldecyl 2-phenylacetate, 2-hexyl-2- methyldecyl 4-phenylbutanoate, 2-hexyl-2-methyldecyl 5-phenylpentanoate, 2-hexyl-2-methyldecyl 6-phenylhexanoate, 2-hexyl-2-methyldecyl 7-phenylheptanoate, 2-hexyl-2-methyldecyl 2-methylcyclohexane-1-carboxylate, 2-hexyl-2-methyldecyl 3-methylcyclohexane-1-carboxylate, 2-hexyl-2-methyldecyl 4-methylcyclohexane-1-carboxylate, 2-hexyl-2-methyldecyl 4-(tert-butyl)cyclohexane-1-carboxylate, 2-hexyl-2-methyldecyl 4-phenylcyclohexane-1-carboxylate, 2-hexyl-2-methyldecyl 4-pentylcyclohexane-1-carboxylate;

2-decyl-2-methyltetradecyl acetate, 2-decyl-2-methyltetradecyl propanoate, 2-decyl-2-methyltetradecyl butanoate, 2-decyl-2-methyltetradecyl pentanoate, 2-decyl-2-methyltetradecyl hexanoate, 2-decyl-2-methyltetradecyl octanoate, 2-decyl-2-methyltetradecyl decanoate, 2-decyl-2-methyltetradecyl dodecanoate, 2-decyl-2-methyltetradecyl tetradecanoate, 2-decyl-2-methyltetradecyl hexadecanoate, 2-decyl-2-methyltetradecyl octadecanoate, 2-decyl-2-methyltetradecyl icosanoate, 2-decyl-2-methyltetradecyl benzoate, 2-decyl-2-methyltetradecyl 4-methylbenzoate, 2-decyl-2-methyltetradecyl 4-ethylbenzoate 2-decyl-2-methyltetradecyl 4-butylbenzoate, 2-decyl-2-methyltetradecyl 4-pentylbenzoate, 2-decyl-2-methyltetradecyl 4-hexylbenzoate, 2-decyl-2-methyltetradecyl 4-heptylbenzoate, 2-decyl-2-methyltetradecyl 4-octylbenzoate, 2-decyl-2-methyltetradecyl [1,1'-biphenyl]-4-carboxylate, 2-decyl-2-methyltetradecyl 1-naphthoate, 2-decyl-2-methyltetradecyl 2-naphthoate, 2-decyl-2-methyltetradecyl-3-phenylpropanoate, 2-decyl-2-methyltetradecyl 2-phenylacetate, 2-decyl-2-methyltetradecyl 4-phenylbutanoate, 2-decyl-2-methyltetradecyl 5-phenylpentanoate, 2-decyl-2-methyltetradecyl 6-phenylhexanoate, 2-decyl-2-methyltetradecyl 7-phenylheptanoate, 2-decyl-2-methyltetradecyl 2-methylcyclohexane-1-carboxylate, 2-decyl-2-methyltetradecyl 3-methylcyclohexane-1-carboxylate, 2-decyl-2-methyltetradecyl 4-methylcyclohexane-1-carboxylate 2-decyl-2-methyltetradecyl 4-(tert-butyl)cyclohexane-1-carboxylate, 2-decyl-2-methyltetradecyl 4-phenylcyclohexane-1-carboxylate, and 2-decyl-2-methyltetradecyl 4-pentylcyclohexane-1-carboxylate.

The neo-alcohol-derived ester compounds of this disclosure can have many applications. One contemplated application is as a base stock of a lubricating oil composition described in detail below. The neo-alcohol-derived ester compounds of this disclosure can also find use in other fields such as plasticizers, personal care products, heat transfer fluids, hydraulic power transfer oils, processing oils, and the like.

In the neo-alcohol-derived ester compound of this disclosure, there is a quaternary carbon atom at the beta location to the ester group. Without intending to be bound by any theory, it is believed that the presence of this quaternary carbon leads to higher oxidation stability at high temperature of the molecule compared to a similar ester having a hydrogen atom ("beta-hydrogen") connected to the carbon atom at the beta location. The availability of a beta-hydrogen makes decomposition of the ester compound via a possible six-member ring mechanism (mechanism (a) below), which requires lower energy than the free-radical mechanism necessitated by the quaternary carbon in the neo-alcohol (mechanism (b) below).

(a) Decomposition Via Six-Member Ring Mechanism

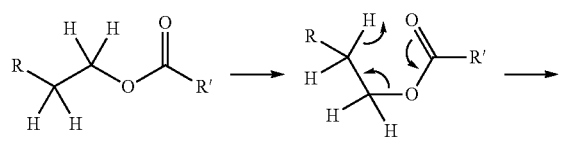

-continued

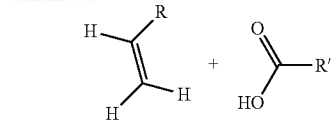

(b) Decomposition Via Free-Radical Mechanism

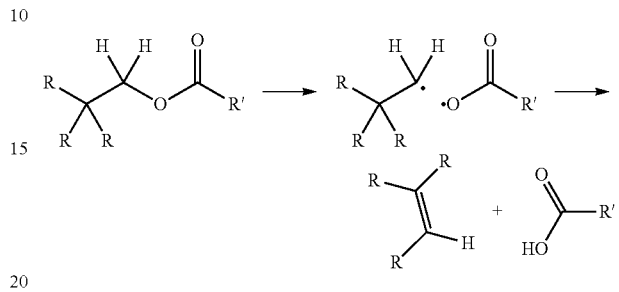

An esters of this disclosure can be a mono-ester derived from a mono neo-alcohol instead of a polyol. Compared to known esters derived from neo-polyols, a mono-ester derived from a mono neo-alcohol of this disclosure tends to have lower polarity. However, the ester group in the molecule imparts higher polarity to the esters of this disclosure than hydrocarbon molecules such as polyalphaolefins. The moderate polarity of a mono-ester of this disclosure can be particularly desirable for blending with polyalphaolefins and polar additives used in a lubricating oil composition of this disclosure.

II. The Lubricating Oil Composition Comprising Ester of this Disclosure

II.1 General

In this disclosure, a lubricating oil formulation means a lubricating oil product ready for its intended use. Thus, examples of lubricating oil formulations include: engine oils ready for putting into the crankcase of an internal combustion engine; gear oils ready for being dispensed into a gear box; greases ready for being applied to apparatus in need of greasing; and the like. In this disclosure, a lubricating oil composition can be any portion or the entirety of a lubricating oil formulation. Thus, a lubricating oil composition can be, for example: (i) a base stock; (ii) an additive package comprising one or more additives; (ii) a mixture of two or more base stocks absent any additive; (iii) a mixture of one or more base stocks with one or more additives but not the entirety of a lubricating oil formulation; and (iv) a lubricating oil formulation in its entirety.

The esters of this disclosure are useful as base stocks in formulating lubricating oil compositions. To make a final lubricating oil formulation as a product, one may add additional components, such as other base stocks, additional quantities of the materials already present in the lubricating oil composition, additive components, and the like, to the lubricating oil composition. A particularly preferred embodiment of the lubricating oil composition of this disclosure; however, is a lubricating oil formulation.

II.2 Lubricating Oil Base Stocks Comprising Neo-Alcohol-Derived Ester

The esters of neo-alcohols of this disclosure have desirable properties such as KV100, KV40, and viscosity index comparable to certain commercial Group V ester-type base stocks. The high polarity of the neo-alcohol-derived ester molecules as a result of the presence of the ester group lends them excellent blending capabilities with many other base stocks, providing needed solvency and dispersancy of polar components such as additives and sludge formed during the service life of the lubricating oil. The exceptionally high oxidation stability of the neo-alcohol-derived ester molecules as a result of the location of the ester group connected to a quaternary carbon atom with no hydrogen directly bonded thereto is particularly desirable for a high-performance lubricating oil formulation which is exposed repeatedly to oxidative environment such as automotive engine oils.

The lubricating oil base stock of this disclosure can comprise a single neo-alcohol-derived ester compound as disclosed above. The concentration of the ester compound in the base stock can be, e.g., at least 80, 90, 95, 98, or even 99 wt %, based on the total weight of the base stock.

The lubricating oil base stock of this disclosure can comprise two or more neo-alcohol-derived esters as disclosed above. Such base stock can be produced by mixing two ester compounds in their substantially pure form, or produced from a single esterification reaction operation by reacting (i) one neo-alcohol with two or more acids, or (ii) two or more neo-alcohols with one or more acids. Such mixed-ester base stock can be particularly advantageous where a mixture of neo-alcohols (preferably, neo-alcohols with similar molecular weights and/or molecular structures) or a mixture of acids (preferably, acids with similar molecular weights and/or molecular structures) can be procured at a lower cost than a pure single-compound neo-alcohol product or acid product.

The lubricating oil base stock of this disclosure desirably has a KV100 in the range from k1 to k2 cSt, where k1 and k2 can be, independently, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, or 40.0, as long as k1<k2. Preferably k1=4.0, and k2=30.0. More preferably k1=5.0, and k2=25.0. Therefore, the base stock of this disclosure has a relatively "low" viscosity at the normal operating temperature of an internal combustion engine lubricating oil.

The lubricating oil base stock of this disclosure desirably has a viscosity index as determined pursuant to ASTM D2270 in the range from v1 to v2, where v1 and v2 can be, independently, −100, −90, −80, −70, −60, −50, −40, −30, −20, −10, 0, 10, 20, 30, 40, 50, 60, 70, 80, 90, 100, 110, 120, 130, 140, 150, 160, 170, 180, 190, 200, 210, 220, 230, 240, 250, 260, 270, 290, or 300, as long as v1<v2. Preferably v1=0, and v2=250. More preferably v1=25, and v2=200. Still more preferably v1=100, and v2=170.

The base stock of this disclosure desirably has a NV value in the range from n1 to n2 wt %, where n1 and n2 can be, independently, 0, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90, as long as n1<n2. Preferably, n1=0 and n2=50. More preferably n1=0 and n2=30. Still more preferably n1=0 and n2=20. Still more preferably n1=0 and n2=16. In general, for the same type of neo-alcohol-derived ester base stock, the larger the molecular weight of the molecule, the lower the NV value. For engine oils and base stocks for them, typically a low NV value is preferred, all other parameters held equal.

The base stock of this disclosure desirably have an aniline value as determined by ASTM D611 of no higher than 30, 25, 20, or 15.

As discussed above, compared to ester base stocks derived from neo polyols, the ester base stock of this disclosure comprising mono neo-alcohol-derived esters of this disclosure tend to have lower polarity, which is conducive to seal compatibility of lubricating oil compositions.

On the other hand, due to the presence of the quaternary carbon atom in the esters of this disclosure, the ester base stock of this disclosure tend to have high oxidation stability, making it particularly desirable for lubricating oil compositions intended for high-temperature operation with exposure to oxygen.

The neo-alcohol-derived ester base stock of this disclosure can be used as a primary base stock or a co-base stock in any lubricating oil formulation. Preferably, the neo-alcohol-derived ester base stock of this disclosure is used as a co-base stock in conjunction with a second base stock designated as a primary base stock. In certain applications, it may be desirable to include two or even more additional base stocks in the lubricating oil formulation, in addition to the neo-alcohol-derived ester base stock of this disclosure. For the convenience of description, the neo-alcohol-derived ester base stock is merely referred to as a generic base stock herein, regardless of its primary base stock or co-base stock designation. The base stock of this disclosure comprising a neo-alcohol-derived ester can be particularly advantageous when used as a co-base stock with a non-polar base stock such as those Group I, II, III, GTL, and Group IV base stocks.

The neo-alcohol-derived ester base stocks of this disclosure are preferably used for formulating automobile engine lubricating oils, preferably those meeting the SAE J300 classification standards. However, it is contemplated that the base stocks of this disclosure may be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

The neo-alcohol-derived ester base stock can be present in the lubricating oil formulation of this disclosure in an amount from about c1 to c2 wt %, based on the total weight of the lubricating oil composition, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, or 95, as long as c1<c2. Preferably c1=3, and c2=50. More preferably c1=5, and c2=30. In general, it is desirable that the lubricating oil composition contains the neo-acid-derived ester base stock as a co-base stock. However, it is also contemplated that the lubricating oil formulation of this disclosure may contain the neo-acid derived ester base stock as a primary base stock, and in an extreme case, the lubricating oil formulation may consist essentially of a neo-acid derived ester base stock and additives.

Owing to the high polarity of the neo-alcohol-derived ester base stocks resulting from the ester group in their molecular structures, the lubricating oil compositions of this disclosure can have an improved additive and sludge solvency and dispersancy compared to other lubricating oil compositions free of ester-type base stocks. In addition, a lubricating oil composition including a neo-alcohol-derived ester base stock can have improved seal compatibility compared to compositions free of ester-type base stocks. Moreover, owing to the presence of the quaternary carbon atom in the molecule structure, the neo-alcohol-derived ester base stock of this disclosure can have a high thermal stability.

II.3 Other Base Stocks Useful in the Lubricating Oil Compositions

A wide range of lubricating oil base stocks known in the art can be used in conjunction with the neo-alcohol-derived ester base stock in the lubricating oil compositions of this disclosure, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalpha-olefins (PAO). Group V base stocks include base stocks not included in Groups I-IV. The table below summarizes properties of each of these five groups.

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | | PAO products | |
| Group V | | All other products not included in Groups I, II, III, and IV | |

Natural oils include animal oils (e.g., lard), vegetable oils (e.g., castor oil), and mineral oils. Animal and vegetable oils possessing favorable thermal oxidation stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in this disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalpha-olefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the neo-alcohol-derived ester category in a minor amount may be useful in the lubricating oil compositions of this disclosure. Additive solvency and seal compatibility characteristics may be further imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following maybe used as a base stock in the lubricating oil of this disclosure as well: (1) one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The lubricating oil compositions of this disclosure can comprise one or more Group I, II, III, IV, or V base stocks in addition to the neo-acid-derived ester base stock. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil compositions of this disclosure, but preferably only those with high quality, e.g., those having a VI from 100 to 120. Group IV and V base stocks, preferably those of high quality, are desirably included into the lubricating oil compositions of this disclosure.

II.4 Lubricating Oil Additives

The lubricating oil composition of this disclosure may additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalpha-olefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Column 39, line 68; (c) U.S. Pat. No. 9,422,497 B2, Column 34, line 4 to Column 40, line 55; and (d) U.S. Pat. No. 8,048,833 B2, Column 17, line 48 to Column 27, line 12, the disclosures of which are incorporated herein in their entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil compositions. Insoluble additives in oil can be dispersed in the lubricating oil compositions of this disclosure.

When lubricating oil compositions contain one or more of the additives discussed above, the additive(s) are blended into the lubricating oil composition in an amount sufficient for it to perform its intended function.

It is noted that many of the additives are shipped from the additive manufacturer as a concentrate, containing one or more additives together, with a certain amount of base oil diluents.

III. Method for Making the Ester Products Comprising Neo-Alcohol-Derived Ester Compounds and Lubricating Oil Base Stock Comprising the Same One aspect of this disclosure relates to a process for making (i) an ester product (such as a lubricating oil base stock) comprising a compound having the following formula (I):

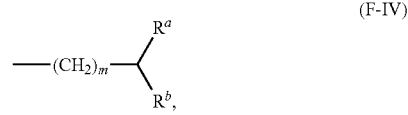

wherein $R^1$ and $R^2$ are each independently a hydrocarbyl group comprising at least two (2) carbon atoms (preferably a C2 to C60 hydrocarbyl group, more preferably a C2 to C60 alkyl group, still more preferably a C2 to C60 linear or branched alkyl group, still more preferably a C2 to C30 linear or branched alkyl group); and $R^3$ is a substituted or unsubstituted hydrocarbyl group, the process comprising: (I) providing a neo-alcohol having a formula (F-II) below:

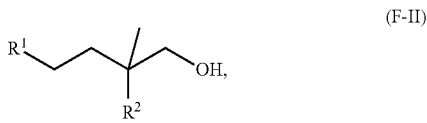

where $R^1$ and $R^2$ are the same as the $R^1$ and $R^2$ in formula (F-I), respectively; and (II) reacting the neo-alcohol with an acid having a formula (F-III) below:

where $R^3$ is the same as the $R^3$ in formula (F-I), and/or an anhydride of the acid, in the presence of an acid catalyst to obtain a product mixture; and (III) obtaining the ester compound and/or the lubricating oil base stock from the product mixture.

It is highly desirable that the acid/anhydride used in the reaction comprises a single mono-acid for the purpose of making a single compound having formula (I), or an ester product (such as a lubricating oil base stock) comprising one or more compound(s) having formula (I), although those of multiple acids can be used as well, especially for the purpose of making an ester product or a lubricating oil base stock which can comprise a mixture of multiple, different compounds each having a molecular structure represented by formula (I).

In formula (F-I), preferably, $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. Preferably c1=2 and c2=30. More preferably c1=2 and c2=24. Still more preferably c1=4, and c2=16. Preferably $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

$$—(CH_2)_m—\overset{R^a}{\underset{R^b,}{\big|}}$$
(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably, $R^a$ and $R^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and IV and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably the total number of carbon atoms in linear $R^1$ and $R^2$ is an even number. Preferably the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably, the total number of carbon atoms in the linear IV and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that IV and $R^2$ contain even number of carbon atoms. It is also particularly preferred that $R^1$ and $R^2$ are identical linear alkyl groups. Where $R^1$ and $R^2$ differ, it is highly desirable that they differ in terms of molar mass thereof by no greater than 145 (or 130, 115, 100, 85, 70, 55, 45, 30, or even 15) grams per mole. Preferably in such cases $R^1$ and $R^2$ differ in terms of total number of carbon atoms contained therein by no greater than 10 (or 9, 8, 7, 6, 5, 4, 3, 2, or even 1).

$R^3$ can be any substituted or unsubstituted hydrocarbyl group. $R^3$ can preferably comprise up to 60, 50, 40, 30, or 20 carbon atoms. Preferably $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Preferably, $R^3$ is a group selected from (a) linear or branched alkyl group, alkylaryl group, aryl group, arylalkyl group, cycloalkyl group, alkylcycloalkyl group, and cycloalkylalkyl group; and (b) substituted derivatives of those in category (a). Substitution to the category (a) hydrocarbyl groups include, but are not limited to: oxygen-containing groups such as alkoxy groups, nitrogen-containing groups, and the like.

$R^3$ can be preferably an alkyl group, an aryl group, an arylalkyl group, an alkylaryl group, a cycloalkyl group, a cycloalkylalkyl group, or an alkylcycloalkyl group.

Non-limiting examples of $R^3$ as an alkyl group include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof.

Non-limiting examples of $R^3$ as an aryl group include phenyl, all naphthyls, all phenanthyls, all indenyls, and the like.

Non-limiting examples of $R^3$ as an alkylaryl group include alkyl-substituted phenyls, alkyl-substituted naphthyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

Non-limiting examples of $R^3$ as an arylalkyl group include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

Preferred examples of aromatic $R^3$ groups are: phenyl, benzyl, 2-phenylethyl, 3-phenylpropryl, 4-phenylbutyl, 3-(3-methylphenyl)propyl, 3-(p-tolyl)propyl, 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, 2-methylcyclohexyl, 3-methylcyclohexyl, 4-methylcyclohexyl, 4-tert-butylcyclohexyl, 4-phenylcyclohexyl, cyclohexylpentyl, nitrophenylmethyl, xylylmethyl, xylylpropyl, methoxyphenylethyl, methoxyphenylpropyl, methoxyphenylbutyl, nitrophenylpropyl, nitrophenylbutyl, and xylylbutyl.

The neo-alcohol product useful in the process for making the ester products of this disclosure can be made from a process comprising the following steps: (I) providing a neo-acid product comprising a neo-acid compound having a formula (F-IIa) below:

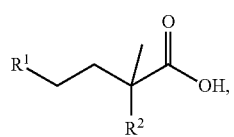

(F-IIa)

and (II) contacting the neo-acid product with a reducing agent under reducing conditions.

The neo-acid product comprising a neo-acid having a formula (F-IIa) above in step (I) above for making the neo-alcohol product can be made by a process comprising (Ia) providing a vinylidene olefin feed comprising a vinylidene olefin having the following formula (F-III):

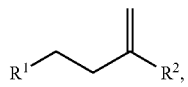
(F-III)

where $R^1$ and $R^2$ correspond to the $R^1$ and $R^2$ in formula (F-I); (Ib) contacting the vinylidene olefin with carbon monoxide in a reactor in the presence of an acid catalyst (preferably at a carbon monoxide partial pressure of at least 1.0 MPa, more preferably at least 3.5 MPa, still more preferably at least 5.0 MPa) to obtain a reaction mixture; (Ic) contacting the reaction mixture with water to obtain an acid product mixture; and (Id) obtaining at least a portion of the neo-acid product from the crude acid mixture.

The vinylidene olefin feed useful in step (Ia) above can be advantageously made from a terminal olefin monomer feed in a process comprising the following steps: (Ia.1) providing a monomer feed comprising a terminal olefin having a formula (F-V) below and a terminal olefin having a formula (F-VI) below: $R^1$—CH=CH$_2$ (F-V); $R^2$—CH=CH$_2$ (F-VI); where $R^1$ and $R^2$ correspond to the $R^1$ and $R^2$ in formulas (F-III), (F-II) and (F-I), respectively; (Ia.2) oligomerizing the monomer feed in an oligomerization reactor in the presence of a catalyst system comprising a metallocene compound to obtain an oligomerization product mixture; and (Ia.3) obtaining at least a portion of the vinylidene olefin feed from the oligomerization product mixture. In this process where $R^1$ and $R^2$ in formula (F-I) of the neo-alcohol are identical, a single terminal olefin having formula (F-V) is used in the monomer feed. Where $R^1$ and $R^2$ in formula (F-I) of the neo-alcohol are different, at least two terminal olefin having different formulas (F-V) and (F-VI) are used in the monomer feed. In case two different terminal olefins are used in the monomer feed, the oligomerization product mixture obtainable from step (Ia.2) may comprise up to four vinylidene olefins as dimers of the two terminal olefins, which may be separated to obtain the desirable vinylidene olefin feed in step (Ia.3) comprising one, two, three, or all four vinylidene olefins, as the case may be. Nine vinylidene olefin dimers can result from three different terminal olefins in the monomer feed. These different vinylidene olefins, if contained in the vinylidene olefin feed in step (Ia) of the process for making the neo-alcohol described above, can be converted into corresponding neo-alcohols in the neo-alcohol product, which, in turn, can be converted into corresponding ester compounds in the neo-alcohol-derived ester product.

The above processes for making neo-alcohol product starting from terminal olefin monomer via the vinylidene olefin intermediate can be illustrated in the following Scheme-I.

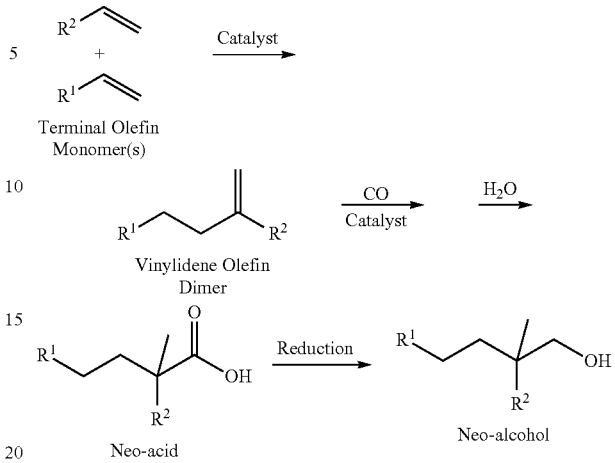

Only one type of vinylidene olefin dimer is illustrated in Scheme-I above. Specific examples of Scheme-I is provided in Part A of the Examples section in this disclosure. Co-pending, co-assigned U.S. Provisional Patent Application No. 62/565,501, entitled "Neo-Alcohol Compounds, Processes for Making Same and Use Thereof" and having a filing date of Sep. 29, 2017/discloses neo-alcohols suitable for making the esters of this disclosure, and processes for making such neo-alcohols, the content of which is incorporate herein by reference in its entirety. Co-pending, co-assigned U.S. Provisional Application Ser. No. 62/565,560, entitled "Neo-Acids and Process for Making the Same" and having a filing date of Sep. 29, 2017 discloses neo-acids suitable for use in the process for making neo-alcohols and processes for making neo-acids, the content of which is incorporated herein by reference in its entirety.

Co-pending, co-assigned U.S. Provisional Application Ser. No. 62/551,081 entitled "Process for Making Vinylidene Olefin" and having a filing date of Aug. 28, 2017, discloses vinylidene olefin dimers of terminal olefins useful for making neo-acids suitable for making neo-alcohols, and processes for making such vinylidene dimers, the content of which is incorporated herein by reference in its entirety.

Non-limiting examples of neo-alcohols useful in the process of this disclosure include the following: 2-ethyl-2-methylhexan-1-ol; 2-methyl-2-propylheptan-1-ol; 2-butyl-2-methyloctan-1-ol; 2-methyl-2-pentylnonan-1-ol; 2-hexyl-2-methyldecan-1-ol; 2-heptyl-2-methylundecan-1-ol; 2-methyl-2-octyldodecan-1-ol; 2-decyl-2-methyltetradecan-1-ol; 2-dodecyl-2-methylhexadecan-1-ol; 2-methyl-2-tetradecyloctadecan-1-ol; and 2-methyl-2-hexadecylicosan-1-ol.

In the carboxylic acid having a formula (F-III), $R^3$ corresponds to the $R^3$ in formula (F-I) as described above.

In the process for making the ester of this disclosure, either the carboxylic acid having a formula (F-III), or its anhydride, or a mixture thereof, can be used to react with the neo-alcohol having a formula (F-II).

Illustrative acids and anhydrides include, for example, aromatic acids, aliphatic acids, glycol ether acids, carboxylic diacids and anhydrides, and the like.

Desirable examples of the carboxylic acid useful in the process of this disclosure are as follows: acetic acid; propanoic acid; butanoic acid; pentanoic acid; hexanoic acid; heptanoic acid; octanoic acid; nonanoic acid; decanoic acid; undecanoic acid; dodecanoic acid; tridecanoic acid; tetradecanoic acid; pentadecanoic acid; hexadecaneoic acid; septadecanoic acid; octadecanoic acid; nonadecanoic acid; icosanoic acid; benzoic acid; 2-methylbenzoic acid, 3-methylbenzoic acid, 4-methylbenzoic acid, 4-butylbenzoic acid, 4-tert-butylbenzoic acid, 4-pentylbenzoic acid, 4-octylbenzoic acid, any dimethylbenzoic acid, any methoxybenzoic acid, any nitrobenzoic acid; phenylacetic acid, 2-methylphenylacetic acid, 3-methylphenylacetic acid, 4-methylphenylacetic acid, 4-butylphenylacetic acid, 4-tert-butylphenylacetic acid, 4-pentylphenylacetic acid, 4-octylphenylacetic acid, any dimethylphenylacetic acid (where the benzene ring is substituted by two methyl groups at any location), any methoxyphenylacetic acid (where the benzene ring is substituted by a methoxy group at any location), any nitrophenylacetic acid (where the benzene ring is substituted by a nitro group); 3-phenylpropanoic acid, 3-(2-methylphenyl)propanoic acid, 3-(3-methylphenyl)propanoic acid, 3-(4-methylphenyl)propanoic acid, 3-(4-butylphenyl)propanoic acid, 3-(4-tert-butylphenyl)propanoic acid, 3-(4-pentylphenyl)propanoic acid, 3-(4-octylphenyl)propanoic acid, any 3-(dimethylphenyl)propanoic acid (where the benzene ring is substituted by two methyl groups at any locations), any 3-(methoxyphenyl)propanoic acid (where the benzene ring is substituted by a methoxy group at any location), any 3-(nitrophenyl)propanoic acid (where the benzene ring is substituted by a nitro group at any location); 4-phenylbutanoic acid, 4-(2-methylphenyl)butanoic acid, 4-(3-methylphenyl)butanoic acid, 4-(4-methylphenyl)butanoic acid, 4-(4-butylphenyl)butanoic acid, 4-(4-tert-butylphenyl)butanoic acid, 4-(4-pentylphenyl)butanoic acid, 4-(4-octylphenyl)butanoic acid, any 4-(dimethylphenyl)butanoic acid (where the benzene ring is substituted by two methyl groups at any locations), any 4-(methoxyphenyl)butanoic acid (where the benzene ring is substituted by a methoxy group at any location), any 4-(nitrophenyl)butanoic acid (where the benzene ring is substituted by a nitro group at any location); 5-phenylpentanoic acid, 5-(2-methylphenyl)pentanoic acid, 5-(3-methylphenyl)pentanoic acid, 5-(4-methylphenyl)pentanoic acid, 5-(4-butylphenyl)pentanoic acid, 5-(4-tert-butylphenyl)pentanoic acid, 5-(4-pentylphenyl)pentanoic acid, 5-(4-octylphenyl)pentanoic acid, any 5-(dimethylphenyl)pentanoic acid (where the benzene ring is substituted by two methyl groups at any locations), any 5-(methoxyphenyl)pentanoic acid (where the benzene ring is substituted by a methoxy group at any location), any 5-(nitrophenyl)pentanoic acid (where the benzene ring is substituted by a nitro group at any location); 5-phenylpentanoic acid, 6-phenylhexanoic acid; 7-phenylheptanoic acid; 8-phenyloctanoic acid; 9-phenylnonanoic acid; 10-phenyldecanoic acid; 2-methylcyclohexane-1-carboxylic acid, 3-methylcyclohexane-1-carboxylic acid, 4-methylcyclohexane-1-carboxylic acid, 4-tert-butylcyclohexane-1-carboxylic acid, 4-phenylcyclohexane-1-carboxylic acid, 5-cyclohexylpentanoic acid; and 2-methyl-1-naphthanoic acid.

Illustrative aromatic acids useful in the process of this disclosure include, for example, benzoic acid, phenyl acetic acid, phenyl propionic acid, phenyl butyric acid, p-tolylacetic acid, xylylacetic acid, tolylpropionic acid, xylylpropionic acid, 4-methoxyphenylacetic acid, methoxyphenylpropionic acid, methoxyphenylbutyric acid, 4-nitrophenylacetic acid, 4-nitrophenylpropionic acid, 4-nitrophenylbutyricacid, xylylbutyric acid, tolylbutyric acid, and the like.

Illustrative aliphatic acids useful in the process of this disclosure include, for example, valeric acid, isovaleric acid, isobutyric acid, hexanoic acid, heptanoic acid, pentanoic acid, 2-ethylhexanoic acid, octanoic acid, isooctanoic acid, nonanoic acid, isononanoic acid, isotridecanoic acid, tetradecanoic acid, stearic acid, isosteric acid, 2-butyloctanoic acid, 2-hexyldecanoic acid, 2-hexyloctanoic acid, 2-butylhexanoic acid, 2-heptylundecanoic acid, 2-octyldecanoic acid, 2-butyldecanoic acid, 2-octyldecanoic acid, 2-decyldodecanoic acid, isotridecanoic acid, 2-butyldodacanoic acid, 2-hexyldecacanoic acid, 2-ethylhexanoic acid, and the like.

Illustrative glycol ether acids useful in the process of this discloser include, for example, methoxyacetic acid, methoxypropionic acid, methoxyethoxyacetic acid, metboxyethoxyethoxyacetic acid, ethoxyacetic acid, ethoxyethoxyacetic acid, ethoxyethoxyethoxyacetic acid, proproxyacetic acid, propoxyethoxyacetic acid, propoxyethoxyetboxyacetic acid, butoxyacetic acid, butoxyethoxyacetic acid, butoxyethoxyethoxyacetic acid, propoxybenzoic acid, and the like.

Illustrative carboxylic diacids useful in the process of this disclosure include, for example, succinic acid, 2-methylsuccinic acid, 2-ethylsuccinic acid, 2-propylsuccinic acid, 2-hexylsuccinic acid, 2-octylsuccinic acid, 2-nonylsuccinic acid, 2-dodecylsuccinic acid, adipic acid, 2-methyladipic acid, 2-ethyladipic acid, 2-propyladipic acid, 2-hexyladipic acid, 2-octyladipic acid, 2-nonyladipic acid, 2-dodecyladipic acid, malonic acid, alkylmalonic acid, azelaic acid, alkylazelaic acid, and the like.

Illustrative carboxylic anhydrides useful in the process of this disclosure include, for example, succinic anhydride, 2-methysuccinic anhydride, 2-ethylsuccinic anhydride, 2-propylsuccinic anhydride, 2-hexylsuccinic anhydride, 2-octylsuccinic anhydride, 2-nonylsuccinic anhydride. 2-dodecylsuccinic anhydride, malonic anhydride, alkylmalonic anhydride, and the like.

Where a diacids and/or anhydride thereof is used in the process for making the ester of this disclosure, a mono-ester and/or a di-ester may be produced as a result of the esterification reaction. It is highly desirable that such selective ester product of this disclosure comprises di-ester. More preferably the selective ester product of this disclosure consists essentially of di-ester(s). Still more preferably the selective ester product of this disclosure consists at least 95 wt % of di-ester(s).

It is highly desirable that a single carboxylic acid or its anhydride having formula (F-III) and a single neo-alcohol are used in the esterification reaction to produce an ester product comprising a single ester compound of this disclosure and/or a lubricating oil base stock comprising a single ester compound of this disclosure. In such case, if an acid/anhydride of a single mono-acid is used, a high-purity ester compound having a formula (F-I) can be obtained and used as a lubricating oil base stock. This is illustrated in Part C of the Examples in this disclosure.

It is also contemplated that multiple carboxylic acids and/or multiple neo-alcohols can be used in the esterification reaction. In such cases multiple ester compounds will be produced. The ratio between the quantities of multiple ester compounds can change as a function of the ratio between the quantities of the multiple neo-alcohols and/or multiple acids used. In certain situations, where a mixture of neo-alcohols having similar molecular weights and structures and/or a mixture of carboxylic acids having similar molecular weights and structures can be procured at a lower cost than a pure neo-alcohol product or a pure carboxylic acid product, this embodiment can be highly economic to produce a mixture of ester compounds with similar molecular structures, molecular weights, and properties suitable as a lubricating oil base stock product.

The anhydrides of the carboxylic acid can be prepared from a corresponding acid having a formula (F-III) by, e.g., dehydration, if not directly available commercially. Dehydration can be achieved by, e.g., reacting with dehydration agents such as $P_2O_5$, followed by separation.

The catalyst used in the reaction can be an acid, desirably a strong acid. Non-limiting examples of such acid are: p-toluenesulfonic acid monohydride (PTSA), titanium isopropoxide and sulfuric acid.

The reaction can be conveniently carried out in the presence of a solvent. The specific solvent used is not critical as long as it is inert in the reaction. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

Reaction conditions for the reaction of the neo-alcohol with one or more acids or anhydrides, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from about 1 to 36 hours, and more preferably from about 2 to 24 hours.

The reaction mixture from the esterification reaction typically comprises the intended ester product(s), water, and one or more of unreacted acid/anhydride and neo-alcohol, and byproducts such as ethers and esters of the acid catalyst. Continuous removal of water from the reaction system can result in higher yield of the ester product. Components in the reaction mixture having a boiling point lower than the intended neo-alcohol-derived ester can be removed by flashing. Depending on the reactants used and reaction conditions, purification methods such as solvent extraction, chromatography, distillation, and the use of sorbents can be carried out to remove byproducts from reaction mixture to finally obtain an ester product of this disclosure comprising a single compound of formula (F-I) or a mixture of multiple compounds of formula (F-I), which can be used as a base stock product, or combined with other, similar compounds to form a base stock product. Preferably, the neo-alcohol-derived ester product obtainable from the process of this disclosure consists essentially of one or more neo-alcohol-derived ester compounds. More preferably, the neo-alcohol-derived ester product obtainable from the process of this disclosure comprises neo-alcohol-derived ester compounds at a total concentration thereof, based on the total weight of the neo-alcohol-derived ester product, at least 95 wt %, or at least 98 wt %, or even at least 99 wt %. Preferably, the neo-alcohol-derived ester product obtainable from the process of this disclosure consists essentially of one predominant neo-alcohol-derived ester compound. More preferably, the neo-alcohol-derived ester product obtainable from the process of this disclosure comprises a predominant neo-alcohol-derived ester compound at a concentration thereof, based on the total weight of the neo-alcohol-derived ester product, of at least 95 wt %, or at least 98 wt %, or even at least 99 wt %.

In particular, the C6-C11 and C12-C18 neo-alcohols produced by the processes of this disclosure can be used as "plasticizer alcohols" and "detergent alcohols," respectively.

This disclosure is further illustrated by the following non-limiting examples.

EXAMPLES

In the following examples, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

Part A: Synthesis of 2-Methyl-2-octyldodecanoic Acid

Example A1: Synthesis of 9-methylenenonadecane

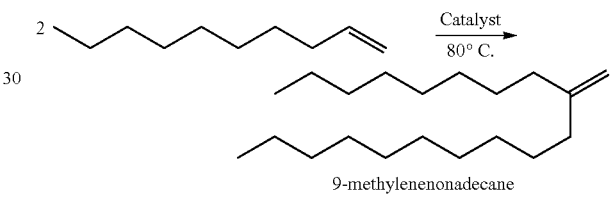

9-methylenenonadecane

Into a batch reactor was charged 5000 grams of 1-decene (98.6% 1-decene, 0.7% 1-octene, 0.7% 1-dodecene), into which 50 grams of 10% MAO solution was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 ml of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and distilled to remove heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

Example A2: Synthesis of 2-Methyl-2-octyldodecanoic Acid

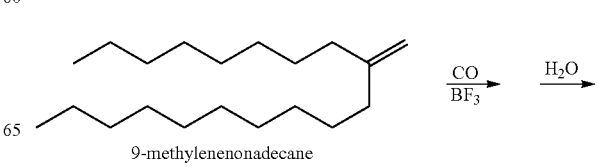

9-methylenenonadecane

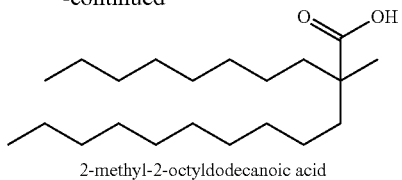

2-methyl-2-octyldodecanoic acid

Into a 1-gallon (3.78-liter) autoclave, 1204 grams of the dimer product obtained from Example B1 above was added. Then 613 grams of BF$_3$-dihydrate was added with stirring and cooling. The reactor was then pressurized to 1000 psig with CO. Afterwards an additional 330 grams of BF$_3$ was bubbled into the reactor. The reactor was then pressurized to 2000 psig (13.79 MPa, gauge pressure) by CO and the temperature of the reactor increased to 50° C. The reaction was allowed to continue for 22 hours at the same CO pressure and the same temperature. Afterwards, the reactor was depressurized and allowed to cool to 30° C.

The reaction mixture was then pressured into a 12-liter flask containing 4 liters of water. Nitrogen gas was bubbled through the mixture for 3 hours to remove residual BF$_3$. Excess water was then drained off. The resultant mixture was then water washed seven (7) times, each time using one (1) liter of deionized water to remove the residual catalyst. Residual water in the resultant mixture was subsequently removed from with a rotary evaporator to obtain a crude product.

The total conversion of the vinylidene olefin in the carboxylation step was measured (by gas chromatography) to be 90.7%, with a yield to heavy dimer species of the vinylidene olefin measured to be 6.6%, and thus a yield to the desired neo-acid product at 84.1%.

The crude product was then batch distilled to remove lights (unreacted vinylidene olefin) and heavies to obtain a final neo-acid product. Gas chromatography of the final neo-acid product showed a concentration of neo-acid of about 98% and a concentration of heavy components of about 2%.

The final neo-acid product was measured to have a KV100 of 8.51 cSt, and a KV40 of 64.0 cSt. $^{13}$C-NMR spectra indicates that the final neo-acid product contained 2-methyl-2-octyldodecanoic acid at a purity of 98.1 wt %.

Part B: Synthesis of 2-Methyl-2-octyldodecan-1-ol

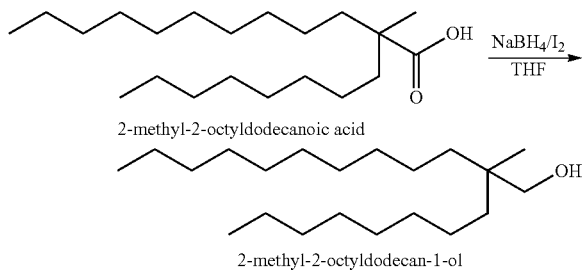

7.0 g NaBH$_4$ was dissolved in anhydrous 75 ml THF in 500 ml four necked round bottom flask with stirring. Then 30 grams of 2-methyl-2-octyldodecanoic acid (MW 326.57, 0.092 mol, made pursuant to Part A of the Examples of this disclosure above) in 50 ml THF solution was added drop wise very slowly over 2 h. The mixture was stirred for 1 hour until hydrogen gas evaluation stops. A solution of iodine (18.7 grams) in 40 ml THF was added drop wise at 10 to 20° C. into a stirred mixture in about 2.5 hours, causing evolution of hydrogen, a significant exothermic and disappearance of red color of iodine. The solution was stirred overnight and heated to reflux for 1 hour. Approximately 50 ml THF was then distilled from the reaction mixture. To the cooled suspension from the residual of the distillation was added 100 ml cyclohexane and 10% NaOH solution. The solution was stirred vigorously until gas evolution ceased and the precipitated material disappeared. The mixture was then transferred into a separatory funnel. The cyclohexane solution thus separated was washed three times with 50 ml 10% NH$_3$ solution and once with 50 ml of 15% NaHSO$_4$ aqueous solution and once with brine solution. Evaporation of solvent gave crude 2-methyl-2-octyldodecan-1-ol. A further distillation under vacuum yielded a final purified product of 2-methyl-2-octyldodecan-1-ol of 25 grams (87%). The final purified product was confirmed by IR and NMR spectra. IR (cm$^{-1}$): 3347, 2925, 2852, 1467, 1377, 1036, 721. $^1$H NMR (CDCl$_3$): δ 3.25 (s, 2H) HO—CH$_2$—), 1.25-1.12 (m, 33H, —CH$_2$—), 0.81-0.74 (m, 9H, CH$_3$). $^{13}$C NMR (CDC$_{13}$): 69.85, 37.25, 36.43, 31.95, 30.69, 29.72, 29.68, 29.38, 23.43, 22.89.4.09.

Part C. Synthesis of 2-Methyl-2-octyldodeccyl Hexanoate

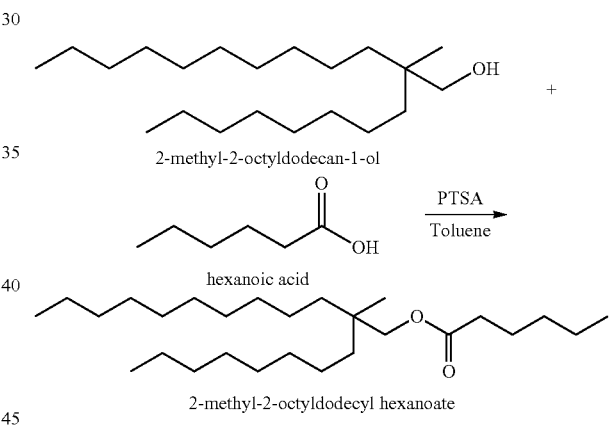

Neo-alcohol 2-methyl-2-octyldodecan-1-ol (7 g, 0.0224 mol, MW: 312.58, made pursuant to Part B of the Examples in this disclosure above), hexanoic acid (5.2 g 0.0224 mol, MW: 116.16) and p-toluenesulfonic acid monohydride (PTSA) (2.13 g, 0.00112 mol, MW: 190.22) were mixed with 75 ml toluene in three necked round bottom flask along with a Dean-Stark water trap apparatus. Then solution was refluxed overnight (18 hours). In 18 hours, about 2-3 ml water was collected in the trap. Toluene was then removed by simple distillation at 50° C. The residual mixture was then extracted by methylene chloride (MC). The extracted product in the MC was washed with water once (100 ml) and 10% aqueous NaHCO$_3$ once (100 ml). Then the MC was evaporated by simple distillation. The residual was processed through flash chromatography with hexane. The Hexane layer was then removed by roto-vap at 60° C. under vacuum to obtain a final ester product. The final ester product was characterized by infrared spectroscopy, $^1$H-NMR, and $^{13}$C-NMR. Yield: 8 grams (88%). IR (cm$^{-1}$): 2956, 2926, 2854, 1740, 1467, 1377, 1244, 1169, 1098, 1008, 721. $^1$H NMR (CDCl$_3$): δ 3.71 (d, 2H, O═C—

CH$_2$—), 2.21 (—CH$_2$—), 1.51 (2H, —CH$_2$—), 1.21 (m, 40H, —CH$_2$—), 0.77 (t, 12H, CH$_3$). $^{13}$C NMR (CDC$_{l3}$): 174.26, 70.64, 36.93, 35.93, 34.46, 31.97, 31.33, 30.56, 29.68, 29.65, 29.63, 29.53, 29.34, 24.33, 22.69, 22.35, 14.10, 31.86.

What is claimed is:

1. A compound having a formula (F-I) below:

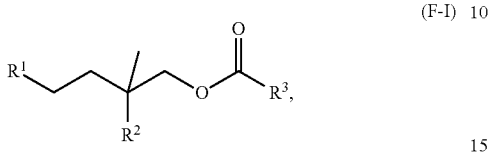

(F-I)

wherein:
R$^1$ and R$^2$ are independently each a hydrocarbyl group comprising at least 2 carbon atoms; and
R$^3$ is a substituted or unsubstituted hydrocarbyl group.

2. The compound of claim 1, wherein R$^1$ and R$^2$ are each independently a C2-C30 linear or branched alkyl group.

3. The compound of claim 1, wherein at least one of R$^1$ and R$^2$ is a linear alkyl group.

4. The compound of claim 3, wherein at least one of R$^1$ and R$^2$ is selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

5. The compound of claim 4, wherein at least one of R$^1$ and R$^2$ is selected from n-butyl, n-hexyl, n-octyl, n-decyl, and n-dodecyl.

6. The compound of claim 1, wherein R$^1$ and R$^2$ are independently each a linear alkyl group.

7. The compound of claim 6, wherein R$^1$ and R$^2$ are independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

8. The compound of claim 1, wherein at least one of R$^1$ and R$^2$ is a branched alkyl group.

9. The compound of claim 8, wherein at least one of R$^1$ and R$^2$ is selected from ethylhexyl, 2-propylheptanyl, 2-butyloctyl, and 3,5-dimethyloctyl.

10. The compound of claim 1, wherein R$^1$ and R$^2$ are identical.

11. The compound of claim 1, wherein R$^3$ is a C1 to C24 group selected from: (a) linear or branched alkyl group, alkylaryl group, aryl group, arylalkyl group, cycloalkyl group, alkylcycloalkyl group, and cycloalkylalkyl group; and (b) substituted derivatives of those in category (a).

12. The compound of claim 11, wherein the category (a) groups are selected from: methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, phenyl, benzyl, 2-phenylethyl, 3-phenylpropryl, 4-phenylbutyl, 3-(3-15 methylphenyl)propyl, 3-(p-tolyl)propyl, 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, 2-methylcyclohexyl, 3-methylcyclohexyl, 4-methylcyclohexyl, 4-tert-butylcyclohexyl, 4-phenylcyclohexyl, cyclohexylpentyl, nitrophenylmethyl, xylylmethyl, xylylpropyl, methoxyphenylethyl, methoxyphenylpropyl, methoxyphenylbutyl, nitrophenylpropyl, nitrophenylbutyl, and xylylbutyl.

13. The compound of claim 1, which is selected from:
2-methyl-2-octyldodecyl acetate, 2-methyl-2-octyldodecyl propanoate, 2-methyl-2-octyldodecyl butanoate, 2-methyl-2-octyldodecyl pentanoate, 2-methyl-2-octyldodecyl hexanoate, 2-methyl-2-octyldodecyl octanoate, 2-methyl-2-octyldodecyl decanoate, 2-methyl-2-octyldodecyl dodecanoate, 2-methyl-2-octyldodecyl tetradecanoate, 2-methyl-2-octyldodecyl hexadecanoate, 2-methyl-2-octyldodecyl octadecanoate, 2-methyl-2-octyldodecyl icosanoate, 2-methyl-2-octyldodecyl benzoate, 2-methyl-2-octyldodecyl 4-methylbenzoate, 2-methyl-2-octyldodecyl 4-ethylbenzoate, 2-methyl-2-octyldodecyl 4-butylbenzoate, 2-methyl-2-octyldodecyl 4-pentylbenzoate, 2-methyl-2-octyldodecyl 4-hexylbenzoate, 2-methyl-2-octyldodecyl 4-heptylbenzoate, 2-methyl-2-octyldodecyl 4-octylbenzoate, 2-methyl-2-octyldodecyl [1,1'-biphenyl]-4-carboxylate, 2-methyl-2-octyldodecyl 1-naphthoate, 2-methyl-2-octyldodecyl 2-naphthoate, 2-methyl-2-octyldodecyl-3-phenylpropanoate, 2-methyl-2-octyldodecyl 2-phenylacetate, 2-methyl-2-octyldodecyl 4-phenylbutanoate, 2-methyl-2-octyldodecyl 5-phenylpentanoate, 2-methyl-2-octyldodecyl 6-phenylhexanoate, 2-methyl-2-octyldodecyl 7-phenylheptanoate;

2-methyl-2-octyldodecyl 2-methylcyclohexane-1-carboxylate, 2-methyl-2-octyldodecyl 3-methylcyclohexane-1-carboxylate, 2-methyl-2-octyldodecyl 4-methylcyclohexane-1-carboxylate, 2-methyl-2-octyldodecyl 4-(tert-butyl)cyclohexane-1-carboxylate, 2-methyl-2-octyldodecyl 4-phenylcyclohexane-1-carboxylate, 2-methyl-2-octyldodecyl 4-pentylcyclohexane-1-carboxylate;

2-butyl-2-methyloctyl acetate, 2-butyl-2-methyloctyl propanoate, 2-butyl-2-methyloctyl butanoate, 2-butyl-2-methyloctyl pentanoate, 2-butyl-2-methyloctyl hexanoate, 2-butyl-2-methyloctyl octanoate, 2-butyl-2-methyloctyl decanoate, 2-butyl-2-methyloctyl dodecanoate, 2-butyl-2-methyloctyl tetradecanoate, 2-butyl-2-methyloctyl hexadecanoate, 2-butyl-2-methyloctyl octadecanoate, 2-butyl-2-methyloctyl icosanoate, 2-butyl-2-methyloctyl benzoate, 2-butyl-2-methyloctyl 4-methylbenzoate, 2-butyl-2-methyloctyl 4-ethylbenzoate, 2-butyl-2-methyloctyl 4-butylbenzoate, 2-butyl-2-methyloctyl 4-pentylbenzoate, 2-butyl-2-methyloctyl 4-hexylbenzoate, 2-butyl-2-methyloctyl 4-heptylbenzoate, 2-butyl-2-methyloctyl 4-octylbenzoate, 2-butyl-2-methyloctyl [1,1'-biphenyl]-4-carboxylate, 2-butyl-2-methyloctyl 1-naphthoate, 2-butyl-2-methyloctyl 2-naphthoate, 2-methyl-2-octyldodecyl-3-phenylpropanoate, 2-butyl-2-methyloctyl 2-phenylacetate, 2-butyl-2-methyloctyl 4-phenylbutanoate, 2-butyl-2-methyloctyl 5-phenylpentanoate, 2-butyl-2-methyloctyl 6-phenylhexanoate, 2-butyl-2-methyloctyl 7-phenylheptanoate, 2-butyl-2-methyloctyl 2-methylcyclohexane-1-carboxylate, 2-butyl-2-methyloctyl 3-methylcyclohexane-1-carboxylate, 2-butyl-2-methyloctyl 4-methylcyclohexane-1-carboxylate, 2-butyl-2-methyloctyl 4-(tert-butyl)cyclohexane-1-carboxylate, 2-butyl-2-methyloctyl 4-phenylcyclohexane-1-carboxylate, 2-butyl-2-methyloctyl 4-pentylcyclohexane-1-carboxylate;

2-hexyl-2-methyldecyl acetate, 2-hexyl-2-methyldecyl propanoate, 2-hexyl-2-methyldecyl butanoate, 2-hexyl-2-methyldecyl pentanoate, 2-hexyl-2-methyldecyl hexanoate, 2-hexyl-2-methyldecyl octanoate, 2-hexyl-2-methyldecyl decanoate, 2-hexyl-2-methyldecyl dodecanoate, 2-hexyl-2-methyldecyl tetradecanoate, 2-hexyl-2-methyldecyl hexadecanoate, 2-hexyl-2-methyldecyl octadecanoate, 2-hexyl-2-methyldecyl icosanoate, 2-hexyl-2-methyldecyl benzoate, 2-hexyl-2-methyldecyl 4-methylbenzoate, 2-hexyl-2-methyldecyl 4-ethylbenzoate, 2-hexyl-2-methyldecyl 4-butylbenzoate, 2-hexyl-2-methyldecyl 4-pentylbenzoate, 2-hexyl-2-methyldecyl 4-hexylbenzoate, 2-hexyl-2-methyldecyl 4-heptylbenzoate, 2-hexyl-2-methyldecyl 4-octylbenzoate, 2-hexyl-2-methyldecyl [1,1'-biphenyl]-4-carboxylate, 2-hexyl-2-methyldecyl 1-naphthoate, 2-hexyl-2-methyldecyl 2-naphthoate, 2-hexyl-2-methyldecyl 3-phenylpropanoate, 2-hexyl-2-methyldecyl 2-phenylacetate, 2-hexyl-2-methyldecyl 4-phenylbutanoate, 2-hexyl-2-methyldecyl 5-phenylpentanoate, 2-hexyl-2-methyldecyl 6-phenylhexanoate, 2-hexyl-2-methyldecyl 7-phenylheptanoate, 2-hexyl-2-methyldecyl 2-methylcyclohexane-1-carboxylate, 2-hexyl-2-methyldecyl 3-methylcyclohexane-1-carboxylate, 2-hexyl-2-methyldecyl 4-methylcyclohexane-1-carboxylate, 2-hexyl-2-methyldecyl 4-(tert-butyl)cyclohexane-1-carboxylate, 2-hexyl-2-methyldecyl 4-phenylcyclohexane-1-carboxylate, 2-hexyl-2-methyldecyl 4-pentylcyclohexane-1-carboxylate;

2-decyl-2-methyltetradecyl acetate, 2-decyl-2-methyltetradecyl propanoate, 2-decyl-2-methyltetradecyl butanoate, 2-decyl-2-methyltetradecyl pentanoate, 2-decyl-2-methyltetradecyl hexanoate, 2-decyl-2-methyltetradecyl octanoate, 2-decyl-2-methyltetradecyl decanoate, 2-decyl-2-methyltetradecyl dodecanoate, 2-decyl-2-methyltetradecyl tetradecanoate, 2-decyl-2-methyltetradecyl hexadecanoate, 2-decyl-2-methyltetradecyl octadecanoate, 2-decyl-2-methyltetradecyl icosanoate, 2-decyl-2-methyltetradecyl benzoate, 2-decyl-2-methyltetradecyl 4-methylbenzoate, 2-decyl-2-methyltetradecyl 4-ethylbenzoate, 2-decyl-2-methyltetradecyl 4-butylbenzoate, 2-decyl-2-methyltetradecyl 4-pentylbenzoate, 2-decyl-2-methyltetradecyl 4-hexylbenzoate, 2-decyl-2-methyltetradecyl 4-heptylbenzoate, 2-decyl-2-methyltetradecyl 4-octylbenzoate, 2-decyl-2-methyltetradecyl [1,1'-biphenyl]-4-carboxylate, 2-decyl-2-methyltetradecyl 1-naphthoate, 2-decyl-2-methyltetradecyl 2-naphthoate, 2-decyl-2-methyltetradecyl 3-phenylpropanoate, 2-decyl-2-methyltetradecyl 2-phenylacetate, 2-decyl-2-methyltetradecyl 4-phenylbutanoate, 2-decyl-2-methyltetradecyl 5-phenylpentanoate, 2-decyl-2-methyltetradecyl 6-phenylhexanoate, 2-decyl-2-methyltetradecyl 7-phenylheptanoate, 2-decyl-2-methyltetradecyl 2-methylcyclohexane-1-carboxylate, 2-decyl-2-methyltetradecyl 3-methylcyclohexane-1-carboxylate, 2-decyl-2-methyltetradecyl 4-methylcyclohexane-1-carboxylate 2-decyl-2-methyltetradecyl 4-(tert-butyl)cyclohexane-1-carboxylate, 2-decyl-2-methyltetradecyl 4-phenylcyclohexane-1-carboxylate, and 2-decyl-2-methyltetradecyl 4-pentylcyclohexane-1-carboxylate.

14. A lubricating oil composition comprising a compound having a formula (F-I) below:

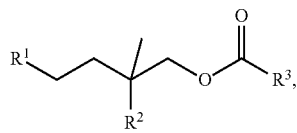

(F-I)

wherein:
$R^1$ and $R^2$ are independently each a hydrocarbyl group comprising at least 2 carbon atoms; and
$R^3$ is a substituted or unsubstituted hydrocarbyl group.

15. A lubricating oil composition of claim 14, which is a lubricating oil base stock.

16. A lubricating oil composition of claim 14, which consists essentially of one or more compounds of the formula (F-I).

17. A lubricating oil composition of claim 14, which is a lubricating oil formulation.

18. A process for making an ester product comprising an ester compound having a formula (F-I) below:

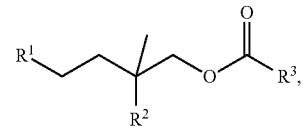

(F-I)

where $R^1$ and $R^2$ are independently each a hydrocarbyl group comprising at least two carbon atoms; and $R^3$ is a substituted or unsubstituted hydrocarbyl group, the process comprising:
(I) providing a neo-alcohol having a formula (F-II) below:

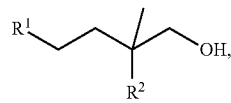

(F-II)

where $R^1$ and $R^2$ are the same as the $R^1$ and $R^2$ in formula (F-I), respectively;
(II) reacting the neo-alcohol with an acid having a formula (F-III) below:

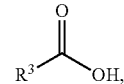

(F-III)

where $R^3$ is the same as the $R^3$ in formula (F-I), and/or an anhydride of the acid, in the presence of an acid catalyst to obtain a product mixture; and
(III) obtaining the ester compound and/or the lubricating oil base stock from the product mixture.

19. The process of claim 18, wherein $R^1$ and $R^2$ are independently each a C2 to C30 linear or branched alkyl group.

20. The process of claim 18, wherein $R^1$ and $R^2$ are independently selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

21. The process of claim 20, wherein $R^1$ and $R^2$ are identical.

22. The process of claim 18, wherein $R^3$ is a C1 to C24 group selected from: (a) linear or branched alkyl group, alkylaryl group, aryl group, arylalkyl group, cycloalkyl group, alkylcycloalkyl group, and cycloalkylalkyl group; and (b) substituted derivatives of those in category (a).

23. The process of claim 22, wherein $R^3$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, phenyl, benzyl, 2-phenylethyl, 3-phenylpropryl, 4-phenylbutyl, 3-(3-methylphenyl)propyl, 3-(p-tolyl)propyl, 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, 2-methylcyclohexyl, 3-methylcyclohexyl, 4-methylcyclohexyl, 4-tert-butylcyclohexyl, 4-phenylcyclohexyl, cyclohexylpentyl, nitrophenylmethyl, xylylmethyl, xylylpropyl, methoxyphenylethyl, methoxyphenylpropyl, methoxyphenylbutyl, nitrophenylpropyl, nitrophenylbutyl, and xylylbutyl.

24. The process of claim 18, wherein the neo-alcohol is selected from:
2-ethyl-2-methylhexan-1-ol; 2-methyl-2-propylheptan-1-ol; 2-butyl-2-methyloctan-1-ol; 2-methyl-2-pentylnonan-1-ol; 2-hexyl-2-methyldecan-1-ol; 2-heptyl-2-methylundecan-1-ol; 2-methyl-2-octyldodecan-1-ol; 2-decyl-2-methyltetradecan-1-ol; 2-dodecyl-2-methylhexadecan-1-ol; 2-methyl-2-tetradecyloctadecan-1-ol; and 2-methyl-2-hexadecylicosan-1-ol; and mixtures and combinations thereof.

25. The process of claim 18, wherein the acid is selected from:
benzoic acid, phenyl acetic acid, phenyl propionic acid, phenyl butyric acid, p-tolylacetic acid, xylylacetic acid, tolylpropionic acid, xylylpropionic acid, 4-methoxyphenylacetic acid, methoxyphenylpropionic acid, methoxyphenylbutyric acid, 4-nitrophenylacetic acid, 4-nitrophenylpropionic acid, 4-nitrophenylbutyricacid, xyxylbutyric acid, tolylbutyric acid;

valeric acid, isovaleric acid, isobutyric acid, hexanoic acid, heptanoic acid, pentanoic acid, 2-ethylhexanoic acid, octanoic acid, isooctanoic acid, nonanoic acid, isononanoic acid, isotridecanoic acid, tetradecanoic acid, stearic acid, isosteric acid, 2-butylhexanoic acid, 2-butyloctanoic acid, 2-hexyldecanoic acid, 2-hexyloctanoic acid, 2-butylhexanoic acid, 2-heptylundecanoic acid, 2-octyldecanoic acid, 2-butyldecanoic acid, 2-octyldecanoic acid, 2-decyldodecanoic acid, isotridecanoic acid, 2-butyldodacanoic acid, 2-hexyldecacanoic acid, 2-ethylhexanoic acid;

methoxyacetic acid, methoxypropionic acid, methoxyethoxyacetic acid, metboxyethoxyethoxyacetic acid, ethoxyacetic acid, ethoxyethoxyacetic acid, ethoxyethoxyethoxyacetic acid, proproxyacetic acid, propoxyethoxyacetic acid, propoxyethoxyetboxyacetic acid, butoxyacetic acid, butoxyethoxyacetic acid, butoxyethoxyethoxyacetic acid, propoxybenzoic acid;

succinic acid, 2-methylsuccinic acid, 2-ethylsuccinic acid, 2-propylsuccinic acid, 2-hexylsuccinic acid, 2-octylsuccinic acid, 2-nonylsuccinic acid, 2-dodecylsuccinic acid, adipic acid, 2-methyladipic acid, 2-ethyladipic acid, 2-propyladipic acid, 2-hexyladipic acid, 2-octyladipic acid, 2-nonyladipic acid, 2-dodecyladipic acid, malonic acid, alkylmalonic acid, azelaic acid, alkylazelaic acid; and mixtures and combinations thereof.

\* \* \* \* \*